US00PP11431P

United States Patent [19]

Cully

[11] Patent Number: Plant 11,431

[45] Date of Patent: Jun. 27, 2000

[54] OAK TREE NAMED 'CLEMONS'

[75] Inventor: Earl Cully, Jacksonville, Ill.

[73] Assignee: Heritage Trees, Inc.

[21] Appl. No.: 09/073,278

[22] Filed: Apr. 28, 1998

[51] Int. Cl.[7] ..... A01H 5/00

[52] U.S. Cl. ..... Plt./225

[58] Field of Search ..... Plt./225

*Primary Examiner*—Howard J. Locker
*Assistant Examiner*—Kent L. Bell

[57] ABSTRACT

A new and distinct cultivar of hybrid oak tree botanically known as *Quercus robur*×*Quercus macrocarpa*, (*Quercus*× *macdanielii*), named 'Clemons', characterized by its great hybrid vigor, straight central leader, pyramidal habit of growth, dark, glossy green disease-resistant foliage, its ability to withstand wind and ice without breakage, and its extreme winter hardiness.

4 Drawing Sheets

The present invention comprises a new and distinct cultivar of hybrid oak tree, botanically known as *Quercus robur*×*Quercus macrocarpa*, (*Quercus*×*macdanielii*), and referred to by the cultivar name 'Clemons'.

The initially discovered tree is growing in a cultivated area on the home grounds of inventor Earl Cully's brother Gene Cully and sister-in-law Ruth Cully, on Rural Route #5, eight miles southeast of Jacksonville, Ill., in Morgan County, in Township 14, Range 10.

The new cultivar 'Clemons' is the result of seed collected in the fall of 1974, from an unnamed hybrid oak, *Quercus robur*×*Quercus macrocarpa*. This parentage was determined by the late Joseph C. McDaniel, Department of Horticulture, University of Illinois. At that time (1974), Dr. McDaniel was considered a leading authority on oak hybrids.

This new oak hybrid had not been described before 1998 when it was written up by Dr. Thomas L. Green, Western Illinois University, Macomb, Ill., and Dr. William J. Hess, The Morton Arboretum, Lisle, Ill., in the summer issue (No. 8) of THE JOURNAL OF THE INTERNATIONAL OAK SOCIETY. It was named in honor of the late Joseph C. McDaniel.

Seedlings grown in 1975 from this unnamed hybrid exhibited characteristics of its parent. Out of this seedling population, approximately one hundred superior one-year-old trees were selected for further evaluation. Of these one hundred hybrid seedlings, only one proved to be worthy of cultivar status. This one hybrid seedling now known as the 'Clemons' cultivar has proven to be extremely outstanding in the twenty-one years it has been under test.

This new oak hybrid is a vigorous grower, maintains a straight central leader to the top of the crown (FIG. 2) and develops a dense, uniformly pyramidal form. It has never suffered breakage from wind or ice in the twenty-one years it has been under test. The tree has dark green, glossy, leathery, tatter-resistant foliage (FIG. 3), and is highly resistant to powdery mildew. The tree is very winter hardy, withstanding winter lows of −28° F. to −33° F. without the slightest damage.

The new hybrid oak has been successfully asexually propagated by chip budding onto *Quercus bicolor* rootstocks. The first asexual propagation was done at Heritage Trees near Jacksonville, Ill., and later at several wholesale nurseries in Oregon. Bud-take has been 85% and 90% when budded onto one year *Quercus bicolor*. No incompatibility between scion and rootstock has been observed. When budded onto one-year rootstock, the tree will grow five to six feet, lightly branched, in one growing season. When budded onto two-year rootstock, the new tree will grow six to eight feet in one growing season and be lightly branched.

The following characteristics in combination distinguish 'Clemons' from other oak species and oak hybrids known to me.

1. Compared to *Quercus robur*, this new hybrid is far more winter hardy, withstanding temperatures of −28° F. to −33° F. without the slightest damage. During October 1991, temperatures were warm for the entire month, then dropped into the 'teens on October 31. On Nov. 3, a record low temperature of −1° F. was recorded. Many tree species were badly damaged and some were killed to the ground, including some english oak *Quercus robur*. The new hybrid did not suffer the slightest damage. Based on the new hybrid's tolerance to this freak blast of arctic air and other winter lows of −28° F. to −33° F., this oak hybrid would be reliably hardy in Zone 4B and the lower half of Zone 4A (USDA Plant Hardiness Zone Map).

2. The new oak hybrid exhibits great hybrid vigor, especially during its early years when grown under optimum conditions. Depending on site, growth rate is several feet a year.

3. The new oak hybrid is a very strong tree. In the twenty-one years it has been under test, it has never lost a limb or suffered even the slightest damage from wind or ice.

4. The new oak hybrid grows with a straight central leader (FIG. 2) and does not require staking, as is the case with many other oaks.

5. The new oak hybrid has dark green, tatter-resistant foliage, which is highly resistant to powdery mildew (FIG. 3).

The new hybrid oak can be compared to the parent tree. Trees of the new hybrid oak differ from the parent tree in growth habit, are more resistant to powdery mildew, and have glossier foliage.

BRIEF DESCRIPTION OF THE DRAWINGS

The accompanying colored photographs illustrate the overall appearance and color of the new oak tree hybrid, showing the colors as true as it is reasonably possible to obtain in colored reproductions of this type. Actual bark and foliage colors may differ in the photographs due to light reflection. Color references made are to The Royal Horticultural Society Colour Chart except where general terms of ordinary significance are used.

FIG. 1—shows the tree in summer foliage.

FIG. 2—shows the branching structure and the straight central leader.

FIG. 3—shows the dark green foliage at actual size.

FIG. 4—shows a 4" caliper grafted tree.

DETAILED BOTANICAL DESCRIPTION

Name: Cultivar 'Clemons'.

Parentage: Self pollination of an unnamed *Quercus robus*× *Quercus macrocarpa* tree.

The plant has been asexually reproduced from: Chip budding and grafting. At this date, rooting of cuttings have not been successful.

Form: Tree.

Shape: Excurrent, pyramidal.

Height: 12.0 m (40').

Spread: 11.9 m (39').

Trunk size: 44.5 cm (17.5") DBH (diameter at breast height).

Base: Cylindrical.

Bark: Bark gray-green; small rectangular blocks, vertical alignment. R.H.S. 197B & 197C, 201A & 201B.

Growth rate: Moderate to fast, depending on site.

Strength: Excellent.

Branches:

*Angle of attachment.*—Most branches 30° and 40° with a range from 25° to 70°; wider angles low in the tree and narrow angles high.

*Spacing.*—Regular.

*Lenticels.*—Small, scattered, not prominent.

Leaves:

*Color.*—Upper surface is between R.H.S. 139A and 139B. Lower surface is between R.H.S. 138A and 138B. Fall color; upper and lower surfaces are close to 162A.

*Length.*—6–14.5 cm, average 11.2 cm.

*Width.*—4–10.5 cm, average 7.5 cm.

*Veins.*—R.H.S. 154A and 154C.

*Form.*—Obovate to oblong-obovate; base cuneate to rounded to auriculate; apex broadly acute to obtuse to rounded lobe, on occasion retuse.

*Margin.*—Coarsely lobed with five to seven pairs of entire usually obtuse lobes; sinus depth varies from shallow to one-half inch in depth to midrib; most one-third inch or less in depth to midrib.

*Texture.*—Leathery; glossy; glabrous above, grayish tomentose beneath

Petiole:

*Length.*—0.6–1.6 cm, average 1.1 cm.

*Color.*—R.H.S. 154A and 154C.

Fruit: Single or double on peduncles 2.7–6.0 cm. long.

*Acorn cap.*—base conic, 2 mm; length average 1.4 to 1.7 cm average 1.5 cm; width 1.8–2.2 cm, average 2.0 cm; silvery tomentum, R.H.S. 199C, scales form short adpressed awns, giving cap a warty appearance; cap covers half of acorn.

*Acorn.*—broadly ovoid to elliptical with golden tomentum, R.H.S. 165C; length 1.8–2.7 cm, average 2.2 cm; width 1.4–2.0 cm, average 1.6 cm; apex 2 mm.

Buds: (vegetative), small 2–3 mm, blunt, reddish-brown.

Flowers: Typical of the species.

It is claimed:

1. A new and distinct cultivar of hybrid oak tree named 'Clemons' as illustrated and described.

* * * * *

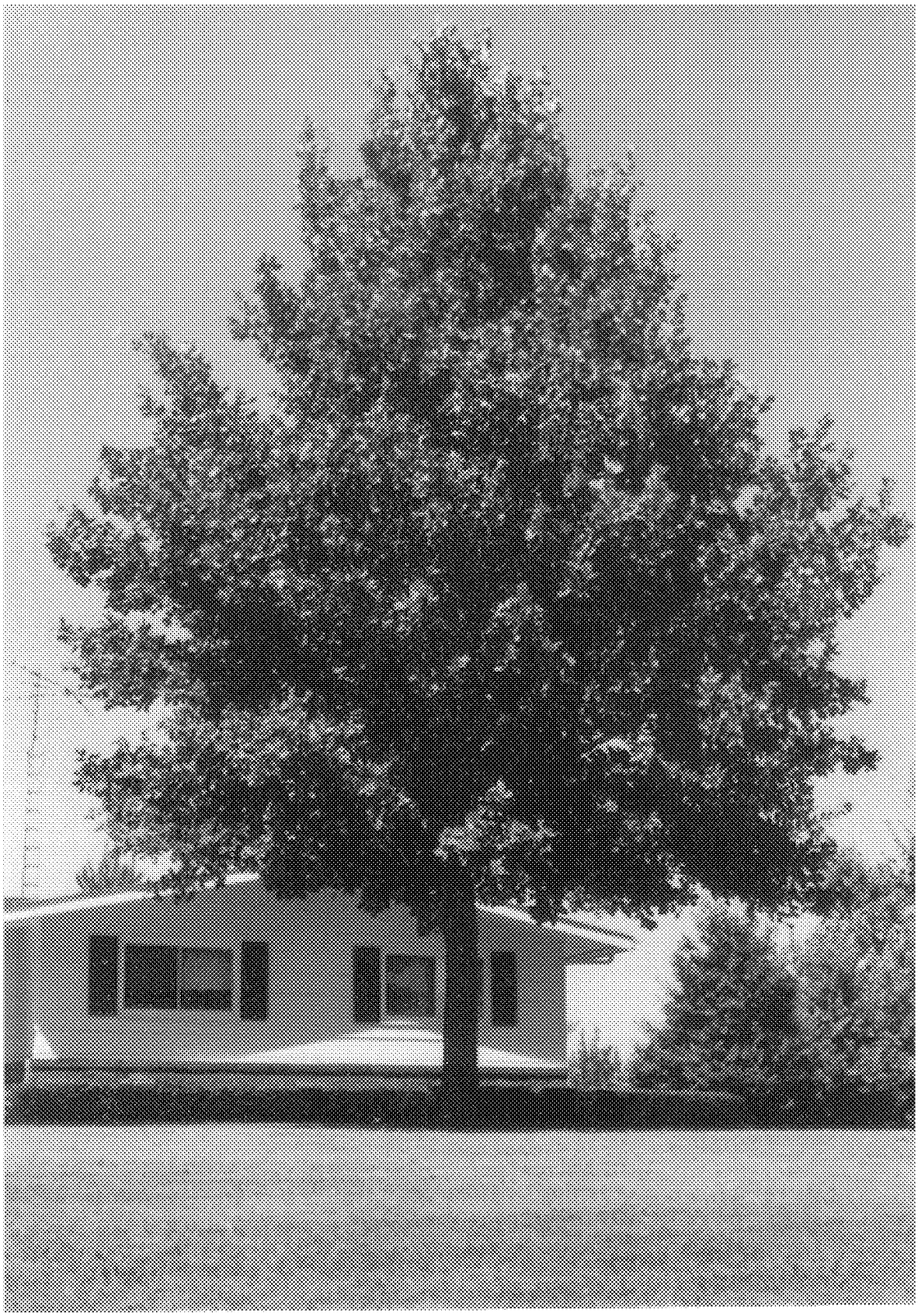
Figure #1

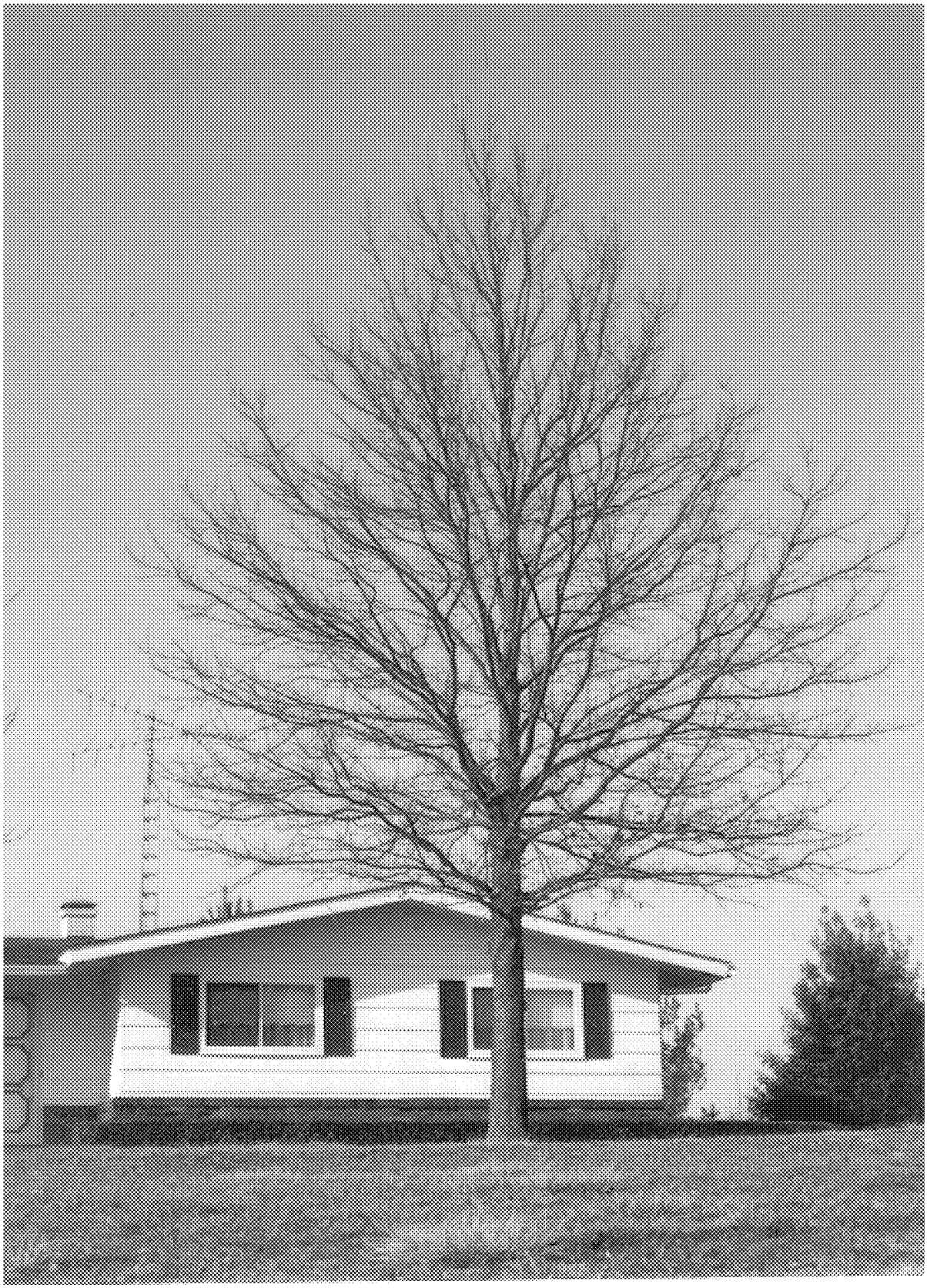
Figure #2

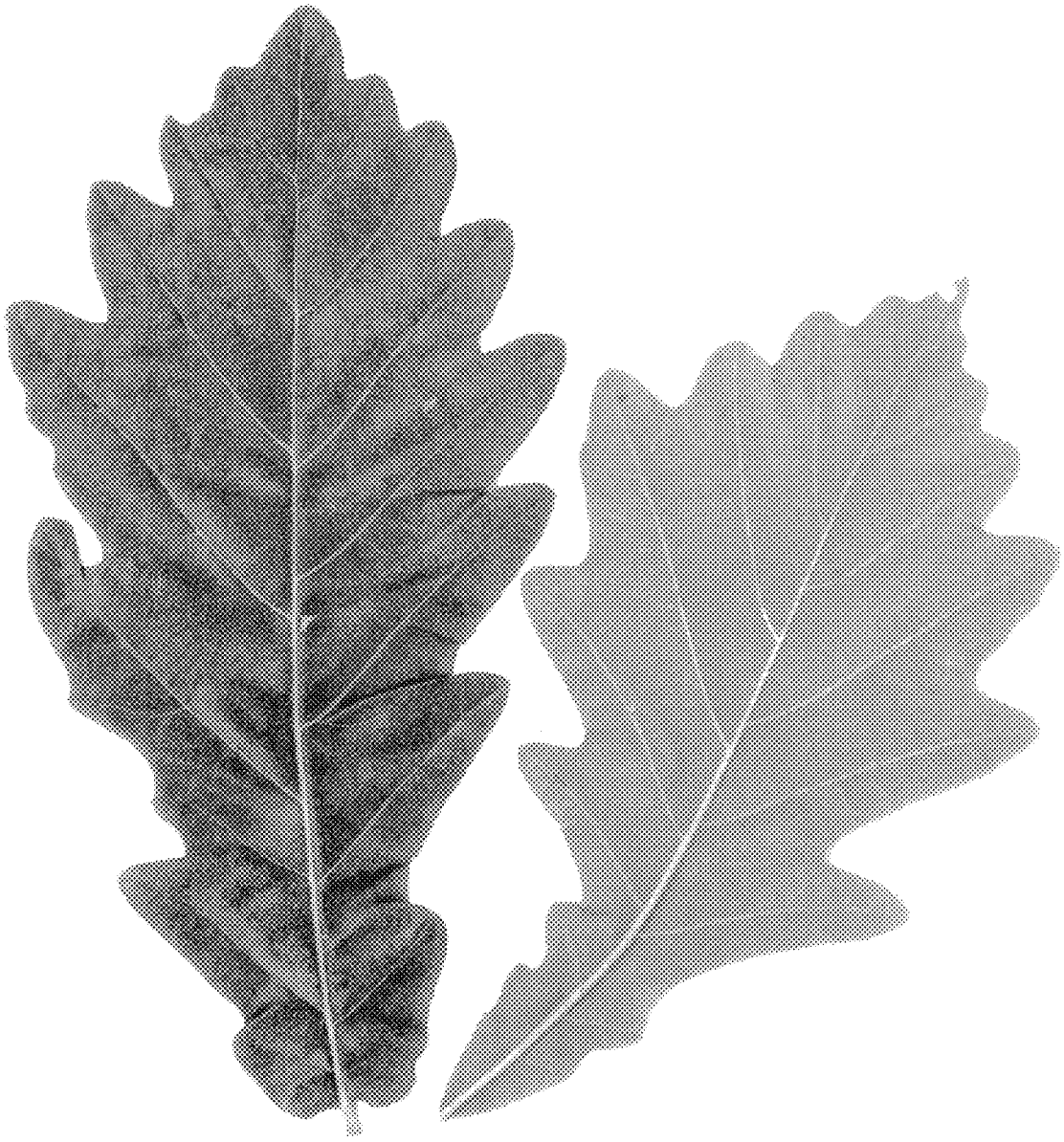
Figure #3

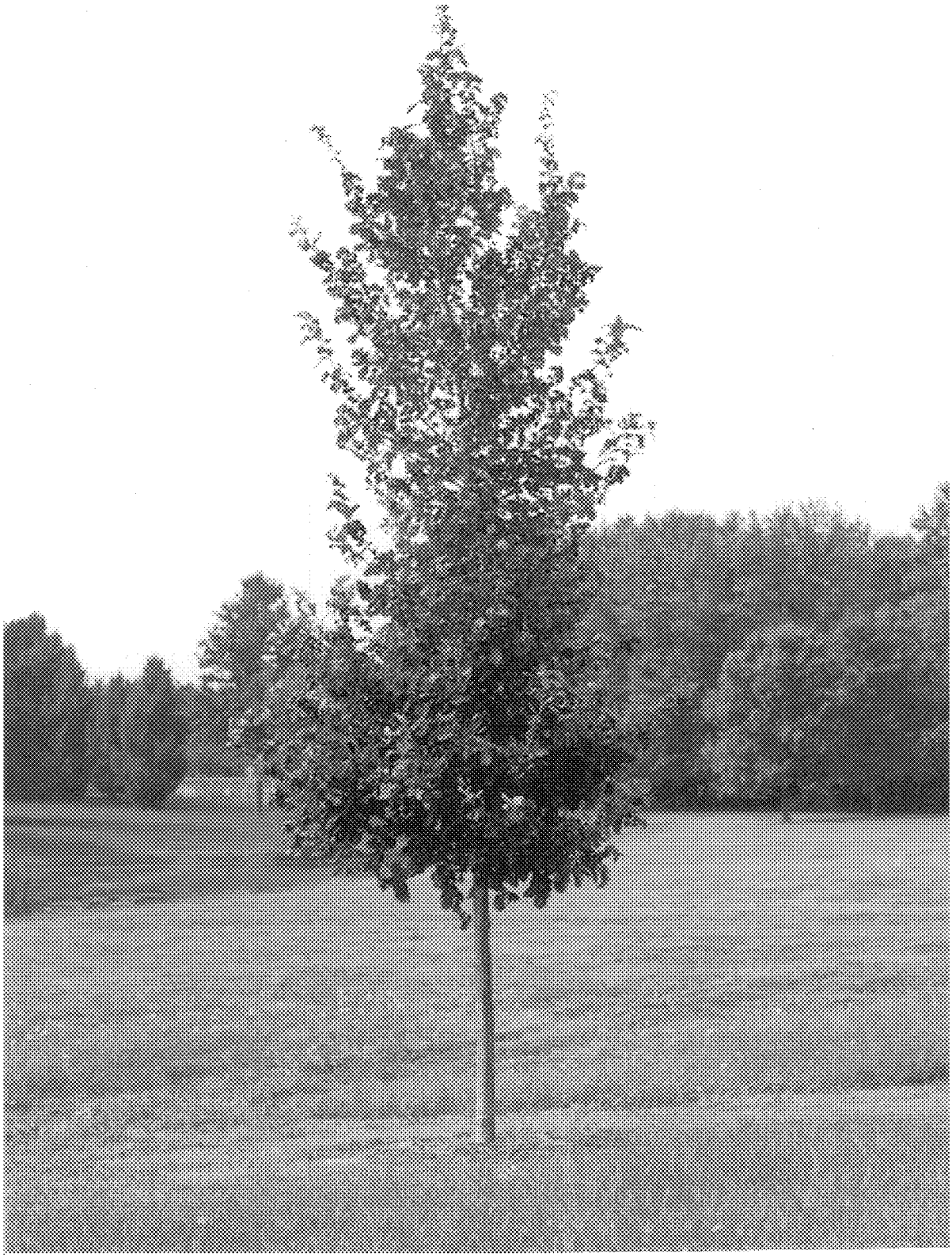
Figure #4